(12) United States Patent
Drake

(10) Patent No.: US 7,850,679 B2
(45) Date of Patent: Dec. 14, 2010

(54) MITRAL HOOK

(76) Inventor: Daniel H. Drake, 2793 Forest Lodge Dr., Traverse City, MI (US) 49684

( * ) Notice: Subject to any disclaimer, the term of this patent is extended or adjusted under 35 U.S.C. 154(b) by 490 days.

(21) Appl. No.: 11/853,826

(22) Filed: Sep. 12, 2007

(65) Prior Publication Data
US 2009/0069888 A1 Mar. 12, 2009

(51) Int. Cl.
*A61F 2/24* (2006.01)
*A61B 17/00* (2006.01)

(52) U.S. Cl. .......................... 606/1; 623/1.3
(58) Field of Classification Search .......... 606/1, 606/48, 171
See application file for complete search history.

(56) References Cited
U.S. PATENT DOCUMENTS

| | | | | |
|---|---|---|---|---|
| 2,738,790 A * | 3/1956 | Todt, Sr. et al. | ............. | 606/145 |
| 4,983,179 A * | 1/1991 | Sjostrom | ..................... | 606/180 |
| 6,129,758 A * | 10/2000 | Love | ......................... | 623/2.11 |
| 2004/0116843 A1* | 6/2004 | Chan | ............................. | 604/2 |
| 2007/0010812 A1* | 1/2007 | Mittelstein et al. | ............ | 606/48 |
| 2008/0119882 A1* | 5/2008 | Cox | ........................... | 606/171 |
| 2008/0132895 A1* | 6/2008 | Clark | .......................... | 606/79 |

* cited by examiner

Primary Examiner—Henry M Johnson, III
Assistant Examiner—Jeffrey B Lipitz
(74) Attorney, Agent, or Firm—John A. Artz

(57) ABSTRACT

A mitral hook instrument for use particularly in heart valve operations. The mitral hook is used in particular for grasping or hooking secondary chords for lysis procedures. The interior surface of the hook has a groove or channel to facilitate use of a scalpel to cut a chord or other member which has been grasped and exposed by the hook. Also, markings are preferably provided on the distal end of the mitral hook instrument in order to assist the surgeon.

20 Claims, 2 Drawing Sheets

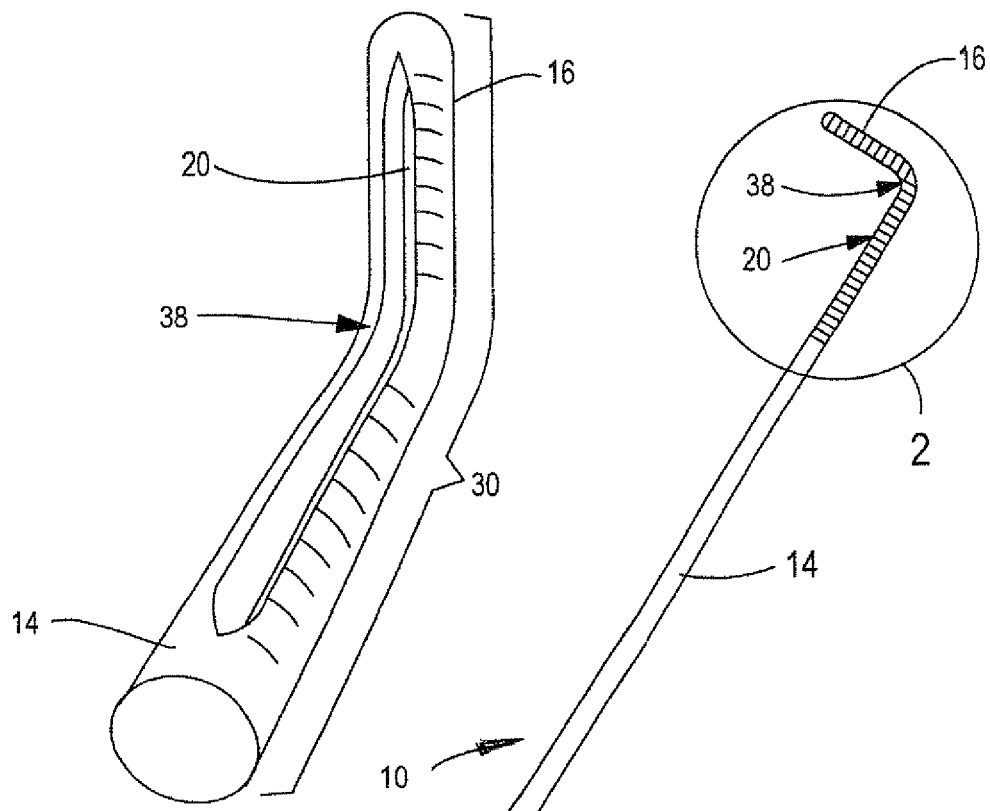
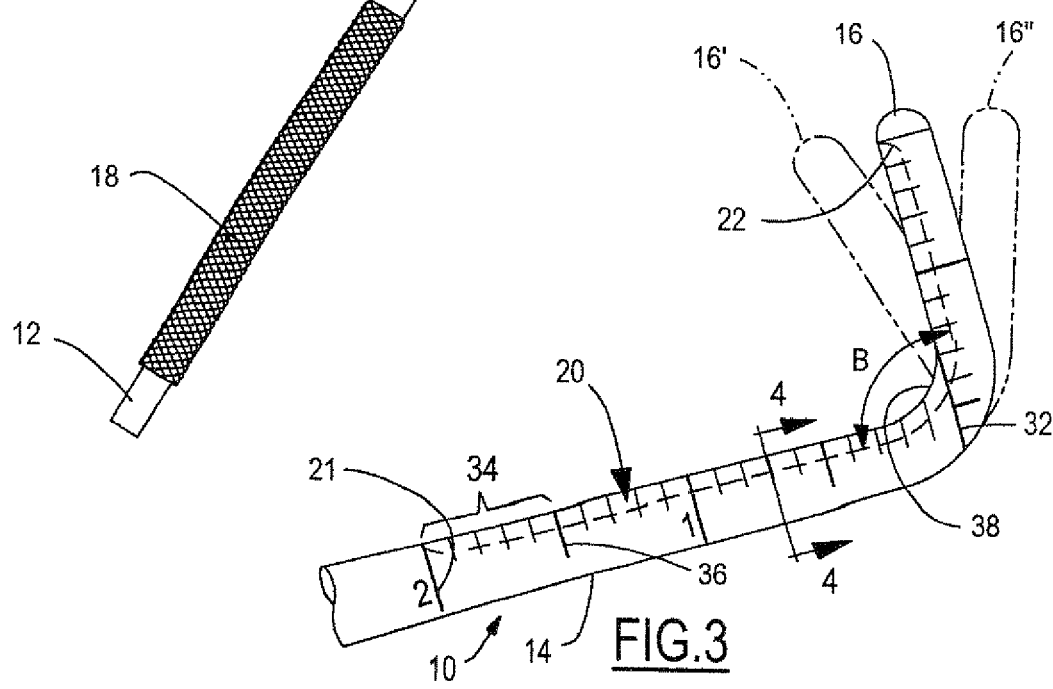
FIG.1 FIG.2 FIG.3

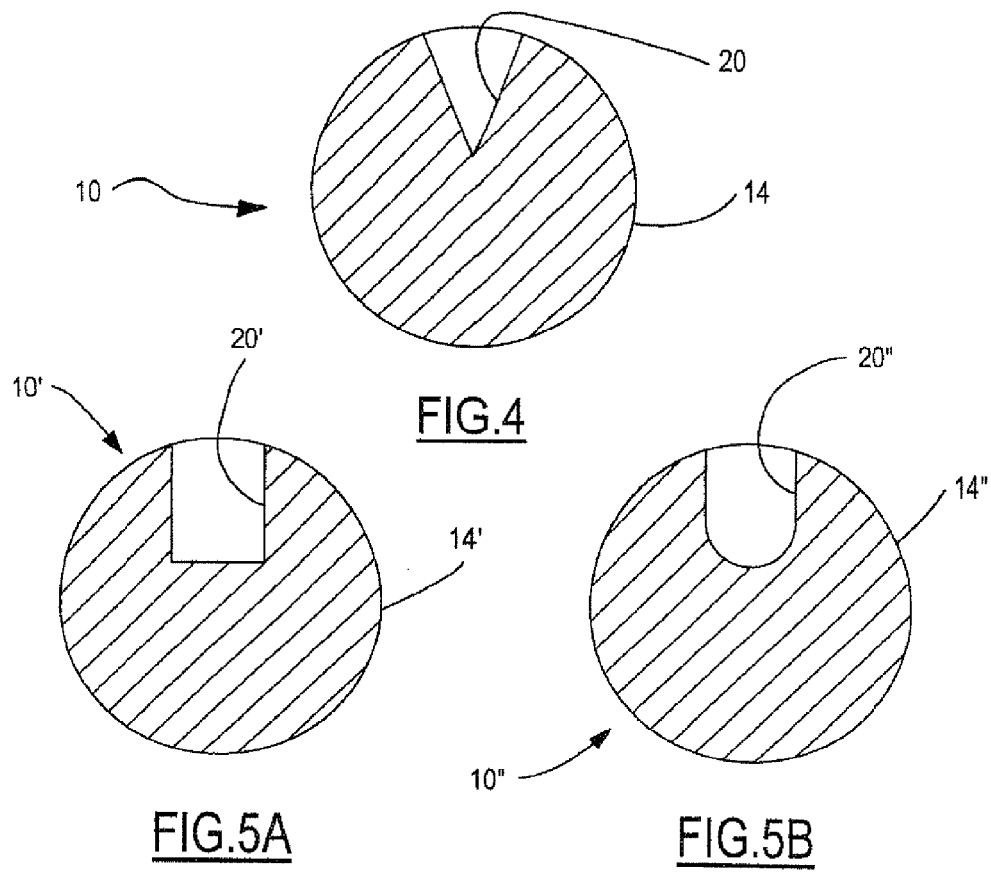
FIG.4
FIG.5A FIG.5B
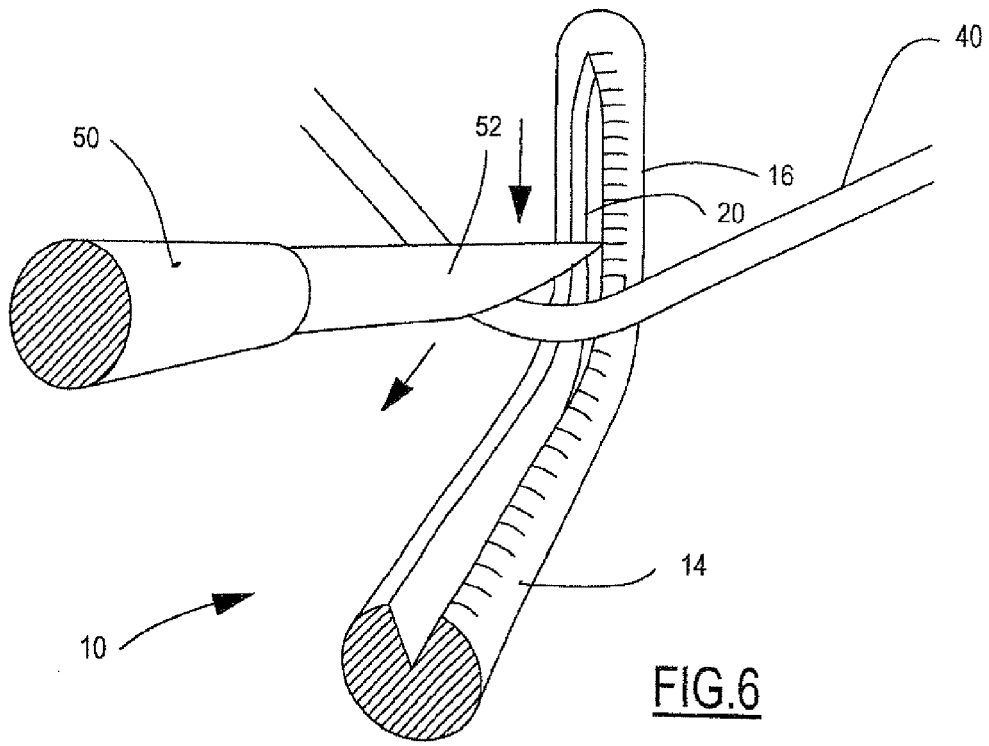
FIG.6

MITRAL HOOK

TECHNICAL FIELD

The present invention relates to instruments for use in medical surgery, and more particularly to specialized instruments used in heart surgery.

BACKGROUND OF THE INVENTION

A malfunction of a person's heart valve, such as mitral regurgitation, can be a life threatening illness. Many systems and techniques have been developed over the years to attempt to correct various heart valve malfunctions. These include full replacement of the valve, the use of annuloplasty rings and bands, and leaflet elongation.

Many procedures and techniques have been utilized by surgeons for heart repair which have allowed patients to return to relatively normal lifestyles. One method and system for treatment of regurgitating heart valves is disclosed, for example, in U.S. patent application Ser. No. 11/752,094, filed on May 22, 2007. Regardless of the technique or procedure utilized, various instruments are used by the surgeons in order to facilitate the valve repair. These instruments include, for example, scalpels and mitral hooks. There is a need for improved instruments and techniques in the heart valve replacement area in order to improve the repair technique and make the surgery easier and less difficult to perform.

It is thus a general object of the present invention to provide improved instruments for use in the repair of heart valves. It is a more specific object of the present invention to provide an improved mitral hook used in the repair of heart valves, particularly regurgitating heart valves.

SUMMARY OF THE INVENTION

The present invention is particularly useful in the correction of regurgitating heart valves, and more particularly in the correction of mitral regurgitation (MR). The present invention, however, can be used in various heart valve repair and/or replacement operations, as well as in other areas of surgery.

In accordance with the present invention, an elongated hook-type instrument is provided, the instrument having a handle end, particularly with a knurled surface, and a tapered distal end terminating in a hook-type or L-shaped member. The instrument has particular use for secondary chord lysis procedures that often are utilized in heart valve repair operations.

The inside surface of the hook at the distal end, as well as the adjacent area on the tapered portion of the instrument shaft, have an elongated groove formed in them. The groove has a size and depth in order to allow the surgeon to place a scalpel in it and slide it along the groove in order to sever secondary chords more easily. The groove can have any cross-sectional shape, but preferably has a substantially V-shape.

A series of gradiations or markings are also positioned along the distal end of the mitral hook instrument. The markings are provided in centimeters and millimeters in order to allow the surgeon to better visualize the situation during the lysis technique.

The mitral hook instrument in accordance with the present invention can be made of a sterilizable, reusable metal material, or can be disposable for use in a single operation.

Further features, benefits and advantages of the inventive process and system will become apparent from the following description of embodiments of the invention, particularly when viewed in combination with the accompanying drawings and appended claims.

BRIEF DESCRIPTION OF THE DRAWINGS

FIG. 1 is a perspective view of an embodiment of the present invention.

FIG. 2 is a close-up of the distal end of the instrument as shown in FIG. 1.

FIG. 3 is another view of the distal end of an embodiment of the invention showing additional features.

FIG. 4 is a cross-sectional view of the embodiment shown in FIG. 3.

FIGS. 5A and 5B illustrate alternate embodiments of the present invention.

FIG. 6 illustrates use of the invention in a secondary chord lysis procedure.

DESCRIPTION OF PREFERRED EMBODIMENTS

The present inventive has particular use and applicability in procedures relative to the repair and replacement of mitral valves in the heart. Mitral valves are often repaired in order to prevent recurrence of mitral regurgitation (MR). The invention will thus be illustrated and described in particular with respect to mitral valve techniques and operations. It is to be understood, however, that the present invention can be used in other surgical operations and procedures in which precise cutting of tissue and string-like tissue members are required.

FIG. 1 is a schematic perspective view of an embodiment of the present invention. The mitral hook instrument is referred to generally by the reference numeral 10. The instrument includes a handle portion 12 at the proximal end and a tapered portion 14 at the distal end. At the termination of the tapered portion, a hook-like end member 16 is provided. In this regard, although the term "hook-like" is utilized relative to the end member 16, the actual shape is closer to the letter "L". For purposes of the present description, however, the end member 16 will be referred to as a "hook".

Mitral hook instruments are known today and are used primarily to "hook" or grasp the secondary chords which are attached to the anterior leaflet of a mitral valve in order to perform secondary chord lysis where desired or appropriate in a heart valve repair or replacement operation. The present invention provides an improved mitral hook instrument particularly for use in such techniques and operations.

The mitral hook instrument 10 is preferably made from a metal material, such as stainless steel or titanium, which can be autoclaved and reused repeatedly in additional heart operations. It is also possible that the mitral hook instrument can be made of a plastic material which can be disposed of after a single use.

The handle portion 12 of the instrument 10 preferably has an outer surface which allows it to be grasped and handled more easily by the surgeon. In the embodiment shown in FIG. 1, the handle has a knurled surface 18.

In accordance with the present invention, a groove or channel 20 is formed on the inside surface of the tapered portion 14 and hook portion 16. As shown in FIG. 4, preferably the groove or channel 20 has a V-shape. The invention is not limited to only V-shaped grooves, however, and the grooves can have other cross-sectional shapes, such as a squared U-shaped groove 20' as shown in FIG. 5A or a rounded U-shaped groove 20" as shown in FIG. 5B. In this regard, FIG. 5A shows an alternate embodiment 10' of the present invention, and a tapered member 14'. FIG. 5B illustrates another embodiment 10' of the present invention having a tapered member 14". Other cross-sectional shapes of the groove or channel can also be utilized in accordance with the spirit and scope of the present invention.

A V-shaped groove is preferred in the sense that it prevents the surgeon's scalpel from dulling less quickly than other cross-sectional shapes of grooves or channels.

The groove 20 also has tapered or slanted end portions 21 and 22 as shown in FIG. 3. This allows the surgeon's scalpel to enter and exit the groove in an easier manner. The slanted lead-ins also help maintain the sharpness of the scalpel and also prevent sharp corners or pockets in the groove or channel which could retain hard-to-clean residue after the operation.

The mitral hook instrument 10 in accordance with the present invention also preferably has a series of gradations or markings 30 thereon. The markings are provided on the distal end of the tapered member 14 and along the hook-like member 16. This is particularly shown in FIGS. 2 and 3.

The markings 30 are preferably indicated in metric units, such as millimeters. In this regard, as shown in FIG. 3, the length of the end or hook member 16 is approximately one centimeter and the markings then proceed up the tapered portion from demarcation line 32 a distance of two centimeters. As shown in FIG. 3, the centimeters are marked by the numbers "1" and "2". The markings 34 in-between the larger markings 36 indicate millimeters.

The centimeter and half centimeters markings are preferably thicker or darker—or have a different color—in order to stand out and allow the surgeon to immediately distinguish between the centimeter markings and the millimeter markings.

Although the markings 30 utilized with the embodiments 10 of the invention as shown in FIGS. 1-4 utilize centimeters and millimeters and have the lengths as shown in FIG. 3, it is also understood that other markings can be utilized of different lengths and different distances along the tapered member 14 and hook member 16.

Also, although the hook member 16 is approximately at the angle B of about 90° relative to the longitudinal axis of the tapered member 14, as shown in FIGS. 1-3, it is also possible to provide the hook member 16 at a more acute or obtuse angle, as shown by phantom lines 16' and 16" in FIG. 3. In this regard, the angle B which preferably is approximately 90°, can range from 45° to 135° and more preferably from 80° to 100°.

As shown in the drawings, the corner or intersection 38 between the tapered member 14 and hook member 16 has a smooth radius to it and is preferably not a sharp corner. This allows the surgeon's scalpel to proceed along the groove in a better manner.

FIG. 6 illustrates use of the mitral hook instrument 10 in a heart valve operation. The instrument 10 is used by the surgeon to grasp or "hook" one of the secondary chord members 40 attached to one of the leaflets of the mitral valve. The surgeon uses the hook to extend the chord through the valve opening in order to cut it. The scalpel member 50 is then used by the surgeon and manually pulled along the groove 20 in order to separate or cut the chord member 40. As shown in FIG. 6, the tip 52 of the scalpel 50 is positioned in the groove or channel 20 and rides along it or is pulled along the groove by the surgeon in order to cut the chord.

When a mitral hook instrument 10 is formed, preferably it is formed in a straight one-piece elongated shape with the portion that is eventually to be made into the hook portion or member 16 formed in the same longitudinal orientation as the tapered member 14. The groove or channel 20 is then cut or formed into the distal end of the tapered member prior to the hook portion being bent to the appropriate angle relative to the longitudinal axis of the tapered member.

The centimeter and millimeter markings 30 are preferably added after the hook member is bent or formed to the appropriate orientation.

While preferred embodiments of the present invention have been shown and described herein, numerous variations and alternative embodiments will occur to those skilled in the art. Accordingly, it is intended that the invention is not limited to the preferred embodiments described herein but instead limited to the terms of the appended claims.

What is claimed is:

1. A mitral hook comprising:
an elongated shaft member having a first end and a second end, said first end having a handle portion and said second end having a hook portion;
said hook portion being bent at an angle to the longitudinal axis of said shaft member and forming an inner surface inside said hook portion and said shaft member and an outer surface outside said hook portion and said shaft member; and
an elongated groove positioned in said inner surface along a portion of said hook portion and along a portion of said shaft member;
said groove having a depth partially through said hook portion and said shaft member;
wherein said groove provides a guide for movement of a scalpel therein and therealong, and allows said scalpel entry anywhere along its length.

2. The mitral hook as described in claim 1 further comprising dimensional markings on said shaft member adjacent said groove.

3. The mitral hook as described in claim 1 wherein dimensional markings are provided on said second end and hook portion at least partially overlapping said groove.

4. The mitral hook as described in claim 2 wherein said dimensional markings are in metric units.

5. The mitral hook as described in claim 2 wherein said dimensional markings have different sizes, shapes, or colors to designate different dimensions.

6. The mitral hook as described in claim 1 wherein said groove has a substantial V-shaped cross-section.

7. The mitral hook as described in claim 1 wherein the cross-sectional shape of said groove is selected from the group comprising V-shaped or U-shaped.

8. The mitral hook as described in claim 1 wherein said groove has tapered lead-in and exit ends.

9. The mitral hook as described in claim 1 wherein said handle portion has a non-skid surface therein.

10. The mitral hook as described in claim 9 wherein said handle portion has a knurled surface.

11. A medical instrument comprising an elongated shaft member, said shaft member having a handle portion at one end and a tapered portion and a hook portion at the other end, and an elongated groove extending along at least a portion of said tapered portion and a portion of said hook portion;
said hook portion being bent at an angle to the longitudinal axis of said handle portion and forming an inner surface inside said hook and tapered portion and an outer surface outside said hook portion; and
an elongated groove positioned in said inner surface along a portion of said tapered portion and a portion of said hook portion;
said groove having a depth partially through said hook portion and said tapered portion;

wherein said groove provides a guide for movement of a scalpel therein and therealong, and allows said scalpel entry anywhere along its length.

12. The medical instrument as described in claim 11 wherein the hook portion is angled relative to the longitudinal axis of said shaft member in the range of 45°-135°.

13. The medical instrument as described in claim 12 wherein said angle is 80°-100°.

14. The medical instrument as described in claim 12 wherein said angle is substantially 90°.

15. The medical instrument as set forth in claim 11 wherein said medical instrument is a mitral hook instrument.

16. The medical instrument as set forth in claim 15 further comprising dimensional markings at least along a portion of said instrument adjacent said groove.

17. The medical instrument as set forth in claim 15 wherein said groove has a substantially V-shape cross-section substantially along its length.

18. The medical instrument as set forth in claim 15 wherein said groove has a tapered lead-in portion at least along one end of said groove.

19. The medical instrument as set forth in claim 18 wherein said groove has tapered lead-in portions at both ends of said groove.

20. The medical instrument as set forth in claim 11 further comprising dimensional markings at least along a portion of said instrument adjacent said groove.

* * * * *